United States Patent
Shipley et al.

(10) Patent No.: US 11,147,952 B2
(45) Date of Patent: Oct. 19, 2021

(54) DRUG COATED INFLATABLE BALLOON HAVING A THERMAL DEPENDENT RELEASE LAYER

(71) Applicant: Medtronic Vascular, Inc., Santa Rosa, CA (US)

(72) Inventors: Adam Shipley, San Rafael, CA (US); Tony Le, Rohnert Park, CA (US); Rajesh Radhakrishnan, Petaluma, CA (US); Terry Morgan, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 343 days.

(21) Appl. No.: 15/141,355

(22) Filed: Apr. 28, 2016

(65) Prior Publication Data

US 2017/0312484 A1    Nov. 2, 2017

(51) Int. Cl.
*A61M 25/10* (2013.01)
*A61L 29/16* (2006.01)
*A61L 29/08* (2006.01)

(52) U.S. Cl.
CPC ........... *A61M 25/10* (2013.01); *A61L 29/085* (2013.01); *A61L 29/16* (2013.01); *A61M 25/104* (2013.01);
(Continued)

(58) Field of Classification Search
CPC ................ A61M 25/10; A61M 25/104; A61M 2025/1075; A61M 2207/00;
(Continued)

(56) References Cited

U.S. PATENT DOCUMENTS

2003/0114791 A1* 6/2003 Rosenthal ................ A61F 2/90
604/96.01
2008/0255509 A1* 10/2008 Wang ................... A61K 31/337
604/103.02
(Continued)

FOREIGN PATENT DOCUMENTS

CN        1526747       9/2004
CN      101589971      12/2009
(Continued)

OTHER PUBLICATIONS

Extended European Search Report for patent application No. EP 17168578.7, dated Sep. 15, 2017; 8 pages.
(Continued)

*Primary Examiner* — Lauren P Farrar
(74) *Attorney, Agent, or Firm* — Mueting Raasch Group

(57) ABSTRACT

A medical device includes an inflatable balloon defining an interior surface and an exterior surface, and a coating including a therapeutic agent disposed on the exterior surface of the inflatable balloon. The coating has a release transition temperature within a range from about 25° C. to about 50° C. When the temperature of the coating is below the release transition temperature, the coating retains at least a portion of the therapeutic agent on the exterior of the inflatable balloon. When the temperature of the coating is above the release transition temperature, the coating releases at least a portion of the therapeutic agent from the exterior of the inflatable balloon.

29 Claims, 4 Drawing Sheets

(52) U.S. Cl.
CPC ..... *A61L 2300/416* (2013.01); *A61L 2420/02* (2013.01); *A61M 2025/105* (2013.01); *A61M 2025/1075* (2013.01); *A61M 2205/0238* (2013.01); *A61M 2205/36* (2013.01); *A61M 2207/00* (2013.01)

(58) Field of Classification Search
CPC ...... A61M 2205/36; A61M 2205/0238; A61M 2025/105; A61L 29/085; A61L 29/16; A61L 2420/02; A61L 2300/416
See application file for complete search history.

(56) References Cited

U.S. PATENT DOCUMENTS

| | | | |
|---|---|---|---|
| 2012/0165786 A1 | 6/2012 | Chappa et al. | |
| 2013/0172815 A1* | 7/2013 | Perry | A61M 25/104 604/103.02 |
| 2014/0343491 A1* | 11/2014 | Slager | A61K 9/1075 604/103.02 |
| 2015/0209489 A1 | 7/2015 | Wang | |
| 2015/0305943 A1* | 10/2015 | Hossainy | A61F 11/002 604/514 |
| 2016/0058915 A1* | 3/2016 | D'Onofrio | A61M 25/104 604/509 |
| 2016/0250387 A1* | 9/2016 | Wang | A61K 31/337 604/103.02 |

FOREIGN PATENT DOCUMENTS

| | | |
|---|---|---|
| CN | 101994253 | 3/2011 |
| CN | 102271750 A | 12/2011 |
| CN | 104857573 | 8/2015 |
| WO | WO 2010/057043 A1 | 5/2010 |

OTHER PUBLICATIONS

Simoes et al., "Modular hydrogels for drug delivery," Journal of Biomaterials and Nanobiotechnology, 2012, 3:185-199.

Hoffman, et al. "Thermally Reversible Hydrogels: II Delivery and Selective Removal of Substances From Aqueous Solutions" Journal of Controlled Release, 4 (1986) 213-222.

Dong et al. "Thermally Reversible Hydrogels: III Immobilization of Enzymes for Feedback Reaction Control" Journal of Controlled Release, 4 (1986) 223-227.

Yoshida et al. "Modulating the Phase Transition Temperature and Thermosensitivity in N-Isopropylacrylamide Copolymer Gels" Journal of Biomaterials Science, Polymer Edition 6:585-598 (1994).

Priest et al. "Lower Critical Solution Temperatures of Aqueous Copolymers of N-Isopropylacrylamide and Other N-Substituted Acrylamides" *Reversible Polymer Gels and Related Systems* 350:255-264 (1987).

Dong et al. "Thermally Reversible Hydrogels" *Reversible Polymer Gels and Related Systems* 350:236-244 (1987).

Tauer et al., "Thermal property changes of poly(N-isopropylacrylamide) microgel particles and block copolymers", *Colloid. Polym. Sci.* (2009) 287:299-312.

Nagahama et al., "Temperature-induced hydrogels through self-assembly of cholesterol-substituted star PEG-b-PLLA copolymers: an injectable scaffold for tissue engineering", *Advanced Functional Materials*, 2008 (18):1220-1231.

Leonenko et al., "Investigation of Temperature-Induced Phase Transitions in DOPC and DPPC Phospholipid Bilayers using Temperature-Controlled Scanning Force Microscopy", *Biophys. J.*, Jun. 2004; 86(6):3783-3793.

Foreign office actions: Chinese Patent Application No. 201110290108.2, filed Apr. 28, 2017; Office Action dated Sep. 28, 2020.

Office action from Chinese Application No. 201710290108.2 dated Jun. 15, 2021, 10 pages.

* cited by examiner

DRUG COATED INFLATABLE BALLOON HAVING A THERMAL DEPENDENT RELEASE LAYER

FIELD

The present disclosure relates to, among other things, inflatable balloon catheters; and more particularly to drug coated inflatable balloon catheters having a thermal dependent release layer.

TECHNICAL BACKGROUND

Vascular atherosclerotic lesions that create arterial luminal narrowing are typically treated in angioplasty procedures via catheters provided with an inflatable balloon. The catheter is advanced, typically following a guidewire, to an opening within the atherosclerotic lesion of the narrowed artery. Once the inflatable balloon has been arranged at the artery narrowing, it may be inflated and deflated, sometimes repeatedly. The inflation, with successive deflation, of the inflatable balloon within the artery can reduce the extent of the arterial luminal narrowing, and restore a suitable blood flow.

In many cases, patients develop a narrowing of the vessel lumen at the intervention point within a few months. Such narrowing, or restenosis, is due to a cell hyperproliferation process, particularly of the vascular smooth muscle cells, probably due to the dilating action caused by the inflatable balloon.

Inflatable balloons can be coated with a drug having anti-proliferative action to prevent or retard restenosis. Among the drugs usually employed to such aim, paclitaxel (taxol) has proved to be particularly efficient.

However, a substantial portion of solid phase paclitaxel disposed on the inflatable balloon is lost to the introducer sheath and distal vasculature during tracking before the inflatable balloon is inflated. Consequently, the drug dose coated onto the inflatable balloon is empirically determined to take this loss into account. However, more efficient retention of drug on the inflatable balloon during tracking while enabling more efficient release of the drug to the vessel wall at the site of treatment would be beneficial to facilitate lower doses of drug on the inflatable balloon, lower systemic drug exposure and providing more uniform distribution of drug across atherosclerotic lesion.

BRIEF SUMMARY

Described herein, among other things, is an inflatable balloon catheter comprising an inflatable balloon on which a coating comprising a therapeutic agent is disposed. The coating is temperature-responsive and is configured to release the therapeutic agent when heated above a release transition temperature. The heating may be passive or active. "Passive" heating refers to heating caused by introducing the coated inflatable balloon from a room temperature environment (e.g., about 23° C.) into a patient at a body temperature environment (e.g., about 37° C.). In such cases, the coating preferably has a release transition temperature between about 25° C. and 37° C. In various embodiments, the inflatable balloon is actively heated during a procedure in which the inflatable balloon catheter is employed. The heating causes the temperature of the coating to rise above a release transition temperature to release the therapeutic agent. In such embodiments, the release transition temperature is preferably above the patient's body temperature so that the therapeutic agent may be retained by the coating on the inflatable balloon until the inflatable balloon is actively heated. Regardless of whether the heating is active or passive, various embodiments of the inflatable balloon catheters described herein enable lower amounts of therapeutic agent to be coated on the inflatable balloon and provide for reduced exposure of distal tissues to the therapeutic agent relative to currently available drug-coated inflatable balloon catheters.

In general, in one aspect, the present disclosure describes a medical device including an inflatable balloon defining an interior surface and an exterior surface, the interior surface defining an interior space, and a coating comprising a therapeutic agent disposed on the exterior surface of the inflatable balloon. The coating has a release transition temperature within a range from about 25° C. to about 50° C. When the temperature of the coating is below the release transition temperature, the coating retains at least a portion of the therapeutic agent on the exterior surface of the inflatable balloon. When the temperature of the coating is above the release transition temperature, the coating releases at least a portion of the therapeutic agent from the exterior surface of the inflatable balloon.

In some embodiments, the coating comprises a first layer disposed on the exterior surface of the inflatable balloon and a second layer disposed on the first layer. The first or second layer may include the therapeutic agent.

In some embodiments, the coating comprises a polymer. The polymer and the therapeutic agent may be intermixed in a layer disposed on the exterior surface of the inflatable balloon.

In some embodiments, the coating has a release transition temperature for the therapeutic agent within a range of about 25° C. to about 50° C. For example, the coating may have a release transition temperature for the therapeutic agent within a range of about 39° C. to about 45° C.

In some embodiments, the coating comprises a temperature-responsive hydrogel.

Examples of temperature responsive hydrogels may include: poly(N-isopropylacrylamide), poly(N'N;-diethylacrylamide), an N-isopropylacrylamide copolymer, an N'N;-diethylacrylamide copolymer, or combinations thereof.

In some embodiments, the coating comprises paclitaxel. The coating may further comprise urea.

In some embodiments, the medical device comprises a heating element configured to actively heat the coating to a temperature above the release transition temperature of the coating.

In some embodiments, a medical device having a coating having a release transition temperature as described herein and a therapeutic agent is used to transfer the therapeutic agent to a patient. The method includes inserting the inflatable balloon of the device to a target location of the patient; inflating the inflatable balloon by introducing a fluid into the interior space of the inflatable balloon; and heating the coating disposed on the inflatable balloon to a temperature at or above the release transition temperature. Inflating the inflatable balloon causes the inflatable balloon to expand against tissue of the patient to transfer the therapeutic agent to the tissue, when the coating is heated at or above its release transition temperature.

In some embodiments, introducing the fluid into the interior space of the inflatable balloon comprises introducing fluid having a temperature greater than the release transition temperature of the coating. Heating the coating may comprise introducing the fluid into the interior space of the inflatable balloon. The fluid introduced into the interior space of the inflatable balloon, in some embodiments, has a temperature of 2° C. or more above the release transition temperature of the coating.

In some embodiments, heating the coating comprises heating a heating element in thermal communication with the coating.

In some embodiments described herein, an inflatable balloon of a medical device is coated with a coating having a release transition temperature as described herein and a therapeutic agent. A method for coating the inflatable balloon comprises applying a coating to an exterior surface of the inflatable balloon. The coating comprises a therapeutic agent and a temperature-responsive polymer and wherein the coating has a release transition temperature within a range of about 25° C. to about 50° C.

In some embodiments, applying the coating comprises applying a composition comprising the polymer on the exterior surface of the inflatable balloon to form a first layer and applying a composition comprising the therapeutic agent on the first layer to form a second layer disposed on the first layer.

In some embodiment, applying the coating comprises applying a composition comprising the therapeutic agent on the inflatable balloon to form a first layer and applying a composition comprising the polymer on the first layer to form a second layer disposed on the first layer.

In some embodiments, applying the coating comprises applying to the exterior surface of the inflatable balloon a composition comprising the therapeutic agent and the polymer.

Advantages and additional features of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, in which.

Figure 1:
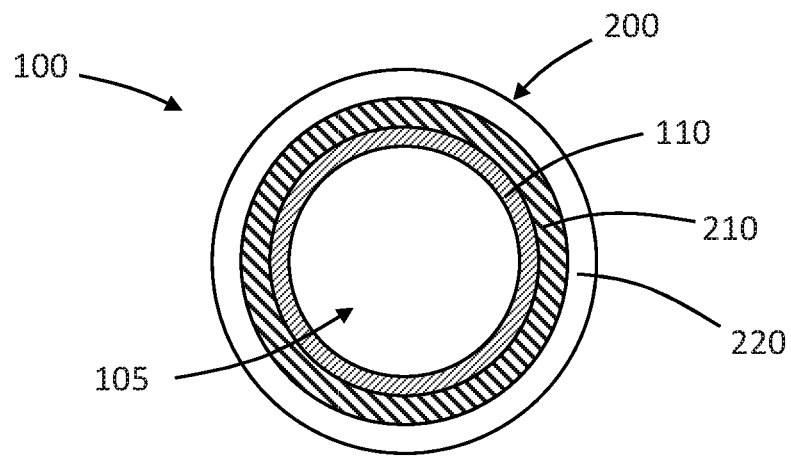
FIGS. 1-3 are schematic sectional views of various embodiments of inflatable balloons having temperature-responsive coatings for releasing therapeutic agent in a temperature-dependent manner.

The schematic drawings are not necessarily to scale.

DETAILED DESCRIPTION

Reference will now be made in greater detail to various embodiments of the subject matter of the present disclosure, some embodiments of which are illustrated in the accompanying drawings. Like numbers used in the figures refer to like components and steps. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components.

The present disclosure describes, among other things, an inflatable balloon catheter comprising an inflatable balloon on which a coating comprising a therapeutic agent is disposed. The coating is temperature-responsive and is configured to retain the therapeutic agent on the inflatable balloon at temperatures below a release transition temperature and to release the therapeutic agent at temperatures at or above the release transition temperature.

The coating may have any suitable release transition temperature. As used herein, "release transition temperature" of a coating means the coating exhibits an abrupt change, as the temperature rises from below to at or above the release transition temperature, in its ability to retain therapeutic agent when in an aqueous environment, such as physiological saline, blood or other bodily fluid. For example and in some embodiments, 30% or less, such as 20% or less or 10% or less, of the therapeutic agent may be released from the coating when the inflatable balloon is inflated and placed in physiological saline at pH 7.4 and a temperature of 5° C. below the release transition temperature for two minutes, while 70% or more, such as 80% or more or 90% or more, of the therapeutic agent may be released from the coating when the inflatable balloon is inflated and placed in physiological saline at pH 7.4 and a temperature of 5° C. above the release transition temperature for two minutes.

The material or materials of the coating may be varied to achieve a desired release transition temperature. In various embodiments, the coating has a release transition temperature in a range from about 25° C. to about 50° C. While a release transition temperatures less than about 37° C. may be below body temperature, it may take some time for the coating on the inflatable balloon to rise from a starting room temperature to body temperature as the device is moved through the patient. Accordingly, a release transition temperature below body temperature may be suitable if the time for the inflatable balloon to reach a target location after being inserted into a patient is fairly short, such as a few minutes or less. A temperature of above 50° C. may be high enough to cause damage to some tissue if the tissue is exposed to such a temperature for an extended period of time. However, because tissue may be in contact with the inflatable balloon for brief periods of time, a release transition temperature of about 50° C. should be well tolerated. In some embodiments, the coating has a release transition temperature in a range from about 37° C. to about 50° C., such as from about 39° C. to about 45° C. In some embodiments, the coating has a release transition temperature in a range from about 25° C. to about 37° C., such as about 30° C. to about 35° C.

When the inflatable balloon is not actively heated, the coating preferably has a release transition temperature of at or less than about 37° C., such as less than about 35° C. When the inflatable balloon is actively heated, the coating preferably has a release transition temperature of at or greater than about 37° C., such as greater than about 39° C.

The coating may include any suitable material or materials. For example, the coating may comprise a temperature-responsive polymer, a material that forms a micelle exhibiting a sol-gel transition, a material having an appropriate melting temperature, or the like.

A coating described herein may comprise any suitable temperature-responsive polymer. For example, a temperature-responsive polymer that becomes soluble in water or becomes a hydrogel at near a transition temperature may be employed. In some preferred embodiments, the coating comprises a temperature-responsive hydrogel. Temperature-responsive hydrogels may release therapeutic agents when highly swollen or swelling and may retain therapeutic agents when not swollen or swelling. Alternatively and depending on the therapeutic agent employed, the responsive hydrogels may retain therapeutic agent when swollen and may expel therapeutic agent when collapsed. Simoes et al., "Modular hydrogels for drug delivery," *Journal of Biomaterials and Nanobiotechnology*, 2012, 3:185-199 is a review on use of responsive hydrogels for drug delivery, which may be useful to provide context for the present disclosure.

Examples of polymers having temperature-responsivity in aqueous environments include poly(N-isopropylacrylamide) (PNIPAA), poly(N'N;-diethylacrylamide) (PDEAA), poly [2-(dimethylamino)ethyl methacrylate] (pDMAEMA) hydroxypropylcellulose, poly(vinylcaprolactame), polyvinyl methyl ether, and the like, and combinations and copolymers thereof. In some preferred embodiments, a coating comprises a temperature-responsive polymer comprising one or both of poly(N-isopropylacrylamide) and poly(N'N;-diethylacrylamide) or copolymers thereof.

Temperature-responsive alkyl acrylamide polymers such as poly(N-isopropylacrylamide) and poly(N'N;-diethylacrylamide) or copolymers thereof transition from a swollen hydrated state to a shrunken dehydrated state when heated above a lower critical solution temperature (LCST) in water. The LCST of such polymers can be tuned according to processes known in the art. For example, copolymerization with a more hydrophilic comonomer can raise the LCST and copolymerization with a more hydrophobic comonomer can lower the LCST. By way of example, N-isopropylacrylamide may be copolymerized with one or more carboxylic acid-containing monomer, such as acrylic acid (AA) or methacrylic acid (MAA), using traditional free radical polymerization techniques to form random copolymers having temperature-responsive properties.

N-isopropylacrylamide-co-acrylamide (NIPAAm-co-AAm) hydrogels may have lower critical solution temperatures (LCST) slightly above body temperature (e.g., above 37° C.). When the temperature of the polymer is raised above its LCST, it undergoes a reversible phase transition, resulting in collapse of the NIPAAm-co-AAm hydrogel structure (see, e.g., A. S. Hoffinan et al. *J. Contr. Rel.* 4:213-222 (1986); and L. C. Dong et al. *J. Contr. Rel.* 4:223-227 (1986)). The collapse forces materials held within the hydrogel matrix to be expelled into the surrounding solution (see, e.g., R. Yoshida et al. *J. Biomater. Sci. Polymer Edn.* 6:585-598 (1994)). Additional information regarding NIPPAm-based polymers is provided in, e.g., J. H. Priest et al. *Reversible Polymer Gels and Related Systems* 350:255-264 (1987); and L. C. Dong et al. *Reversible Polymer Gels and Related Systems* 350:236-244 (1987).

N-isopropylacrylamide-co-AA hydrogels can have a LCST ranging from 32-65° C., depending on the amount of AAm included in the copolymer. A copolymer hydrogel consisting of 95% NIPAAM and 5% AAm has a LCST of approximately 40° C. [see, e.g., J. H. Priest, et al. *Reversible Polymer Gels and Related Systems* 350:255-264 (1987); and L. C. Dong et al. *Reversible Polymer Gels and Related Systems* 350:236-244 (1987)]. Hence, such a copolymer hydrogel is suitable for use in applications where it is desired to cause collapse of the hydrogel at temperatures only slightly above a core human body temperature.

In some embodiments, copolymers of poly(N-isopropylacrylamide) or poly(N'N;-diethylacrylamide) include polyethylene glycol or polystyrene. See, for example, Tauer et al., Thermal property changes of poly(N-isopropylacrylamide) microgel particles and block copolymers, *Colloid. Polym. Sci.* (2009) 287:299-312.

A coating as described herein may comprise any suitable material that has a sol-gel transition at an appropriate temperature (e.g., a release transition temperature discussed above) may be employed. One suitable sol-gel that may be employed is a poly(ethylene glycol)-poly(propylene glycol)-poly(ethylene glycol) triblock copolymer. Another is a cholesterol-substituted star poly(ethylene glycol)-poly(L-lactide) copolymer, which may have a gel transition temperature of about 34° C., as described in Nagahama et al., Temperature-induced hydrogels through self-assembly of cholesterol-substituted star PEG-b-PLLA copolymers: and injectable scaffold for tissue engineering, *Advanced Functional Materials*, 2009 (18):1220-1231.

Additional examples of materials that may be used in a coating as described herein include modified phosphatidylcholine, such as dipalmitoylphosphatidylcholine and dioleoylphosphatidylcholine. Such modified phosphatidylcholine can be used for form micelles that may contain therapeutic agent. For example, the micelles may be sonicated to cause uptake of the therapeutic agent. Such modified phosphatidylcholine can be tuned to have release transition temperatures within desired ranges. For example, dipalmitoylphosphatidylcholine may have a gel-liquid transition temperature between 42° C. and 52° C. See, for example, Leonenko et al., Investigation of Temperature-Induced Phase Transitions in DOPC and DPPC Phospholipid Bilayers using Temperature-Controlled Scanning Force Microscopy, *Biophys. J.*, 2004 June; 86(6):3783-3793. The gel-liquid transition temperature should correspond to the release transition temperature.

The coating may comprise any suitable material having a melting temperature or glass transition temperature within a range of desired release transition temperatures. As the material melts or transitions from a glassy state to a rubber-like state, therapeutic agent may be released. For example, the coating may comprise fats or cholesterols having suitable melting temperatures. By way of another example, the coating may comprise a polymer having a suitable melting temperature or glass transition temperature. The glass transition temperatures of polymers may be tuned according to techniques generally known in the art, such as including plasticizers to reduce glass transition temperatures.

Any suitable therapeutic agent may be included in a coating as described herein. For purposes of the present disclosure, a diagnostic agent, such as a contrast agent or a dye, is a "therapeutic agent." A coating as described herein may include, for example, one or more of an anti-proliferative agent, an antibiotic, an anti-mitotic agent or the like. It will be understood and appreciated that some agents may have more than one therapeutic or diagnostic action. Preferably, a coating as described herein includes an anti-restenosis agent. For example, a coating may include one or more of paclitaxel, rapamycin, everolimus, zotarolimus, and the like.

Other examples of therapeutic agents that may be included in a coating on an inflatable balloon are one or more of heparin or another thrombin inhibitor, hirudin, hirulog, argatroban, D-phenylalanyl-L-poly-L-arginyl chloromethyl ketone or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopidine or another antiplatelet agent; colchicine or another antimitotic, or another microtubule inhibitor; cytochalasin or another actin inhibitor; a remodeling inhibitor; deoxyribonucleic acid, an antisense nucleotide or another agent for molecular genetic intervention; GP IIb/IIIa, GP Ib-IX or another inhibitor or surface glycoprotein receptor; methotrexate or another antimetabolite or antiproliferative agent; an anticancer chemotherapeutic agent; dexamethasone, dexamethasone sodium phosphate, dexamethasone acetate or another dexamethasone derivative, or another anti-inflammatory steroid; dopamine, bromocriptine mesylate, pergolide mesylate or another dopamine agonist; a radiotherapeutic agent; iodine-containing compounds, barium-containing ompounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alphatocopherol, superoxide dismutase, deferoxyamine, a 21-aminosteroid (lasaroid) or another free radical scavenger, iron chelator or antioxidant; and angiopeptin.

Unless content clearly dictates otherwise, general reference to a therapeutic agent in the present disclosure includes reference to salts of the agent, hydrates of the agent, polymorphs of the agent, isomers of the agent (including constitutional isomers and stereoisomers such as enantiomers and diasteriomers), and the like.

The coating may include therapeutic agent particles having any suitable size profile. Preferably, the particulate size profile facilitates uptake by the tissue. Very small particles, such as particles less than 1 μm in size, may be taken up directly into the arterial tissue. In some embodiments the coating includes an agent in a particulate form that has a particle size in a range from 0.01 μm to 20.0 μm. Multimodal ranges, prepared, e.g. by mixing two or more sets of different size ranges may be used in some cases to provide a desired bioavailability profile over time. For example, smaller crystals will more readily dissolve and enter the tissue for immediate effect, while larger crystals will dissolve at a slower rate enabling longer drug persistence.

The coating may include the therapeutic agent in crystalline or amorphous form. In some embodiments, the coating includes an agent in both an amorphous and a crystalline form. In some embodiments, the coating may include an agent in more than one crystalline form.

The coating preferably comprises one or more therapeutic agents in a therapeutically effective amount. As used herein, "therapeutically effective amount" means an agent in an amount capable of inducing a therapeutic or preventive effect against the disease being treated or prevented. For example, if the disease being treated or prevented is restenosis of vascular tissue, the one or more agents present in the coating may be present in an amount effective to treat or prevent restenosis of the treated vascular tissue in the patient.

The coating may comprise one or more therapeutic agents in any suitable density. For example, the therapeutic agent may be present in the coating at a density from about 0.1 μg/mm$^2$ to about 100 μg/mm$^2$, such as between about 0.25 μg/mm$^2$ to about 20 μg/mm$^2$. By way of example, the coating may include paclitaxel in an amount ranging from 1 μg/mm$^2$ to 20 μg/mm$^2$, preferably between 2 μg/mm$^2$ and 7 μg/mm$^2$, more preferably between 3 μg/mm$^2$ and 5 μg/mm$^2$.

In some embodiments, the coating comprises one or more of zotarolamus, sirolimus, dexamethasone and paclitaxel.

Preferably, the coating comprises paclitaxel and is used to treat restenosis. In some embodiments, at least some or all of the paclitaxel is in anhydrous crystalline form. The coating provides for release and bioavailability of a therapeutically effective amount of paclitaxel when the inflatable balloon is expanded, the coating is at or above its release transition temperature and the coating contacts tissue at the site of intervention. Preferably, the coating provides for release from the inflatable balloon surface in periods of time less than 2 minutes, preferably between 30 seconds and 1 minute, and an absorption by the vascular tissue in periods of time ranging between 1 second and 25 minutes, preferably between 20 seconds and 25 minutes.

As used herein, "site of intervention" means the section of the blood vessel treated directly with a catheter inflatable balloon described herein, and the adjacent portion in the tissues of which the post-procedure presence of paclitaxel can be detected. Generally, such section will extend up to 10 mm down- and upstream the contact section with the inflatable balloon.

In some embodiments, a coating comprising paclitaxel also comprises urea. The presence of urea in a paclitaxel-containing coating may promote the release of the paclitaxel. Paclitaxel may be dissolved in an appropriate solvent in the presence of urea and coated on the inflatable balloon, on another coating layer on the inflatable balloon, or mixed with other coating components and coated on the inflatable balloon. Urea may be present in any suitable amount, such as from 1 mg per mL to 100 mg per mL solvent. In some embodiments, a layer of paclitaxel and urea are coated directly on the inflatable balloon or are coated on another layer of the coating.

The coating may include any suitable number of layers. The therapeutic agent may be intermixed with other components of the coating, such as a thermo-responsive material, and applied as a single layer. In some embodiments, a layer comprising therapeutic agent is applied to the inflatable balloon and a layer, for example comprising thermo-responsive material, is applied on top of the therapeutic agent-containing layer. In some embodiments, a layer, for example comprising thermo-responsive material, is applied to the inflatable balloon and a layer comprising the therapeutic agent is applied on top of the previously applied thermo-responsive layer.

In general, a coating layer may be disposed on the inflatable balloon or on a coating layer disposed on the inflatable balloon in any suitable manner. For example, a solution comprising the components of the layer, such as the therapeutic agent or a thermo-responsive polymer, may be coated on the inflatable balloon by dipping the inflatable balloon in the solution, the solution can be sprayed on the inflatable balloon, or the solution can be deposited on the inflatable balloon with, for example, a syringe, micropipette, or other similar dispensing device.

The solution may be applied when the inflatable balloon is inflated, or in a folded condition. If applied when the inflatable balloon is in the folded condition, the solution may penetrate under the folds by capillarity action or may be applied, by for example, micro-nozzles under the folds.

One or more coatings of the solution may be applied to the inflatable balloon or other coating layer. The solvent may be allowed to evaporate under ambient conditions, under heated conditions, under vacuum drying, or heating and vacuum drying. The inflatable balloon or underlying coating layer may be fully or partially coated with the layer or subsequent layer.

Any suitable inflatable medical inflatable balloon may be coated with a thermo-responsive coating described herein. The inflatable balloons may be compliant, semi-compliant or non-compliant. The inflatable balloons may be formed from any suitable material. For example, the inflatable balloons may be formed of polyamides, polyethylene terephathalate (PET), polyurethane, latex, silicone, polyethylene (PE), polypropylene (PP), polyetherimide (PEI), polytetrafluoroethylene (PTFE), ethylene tetrafluoroethylene (ETFE), fluorinated ethylene propylene (FEP), polyoxymethylene (POM), polybutylene terephthalate (PBT), polyether-block-ester, polyvinylchloride (PVC), polyetherblock-amide, polyetheretherketone (PEEK), polyimide (PI), polyphenylene sulfide (PPS), polyphenylene oxide (PPO), poly(ethylene naphthalenedicarboxylate) (PEN), polysulfone, perfluoro(propyl vinyl ether) (PFA), or mixtures, combinations, copolymers thereof, and the like.

The inflatable balloon will typically have a length of at least 1 cm to 50 cm, preferably being in a range from about 1.5 cm to 20 cm, and may have inflated diameters in a range from 1.5 mm to about 20 mm, for instance 1.5 mm to 5 mm, but may be of any suitable size.

An inflatable balloon catheter comprising a coated inflatable balloon as described herein may be used for any suitable purpose. In preferred embodiments, the inflatable balloon catheter is an intravascular inflatable balloon catheter. For example, the inflatable balloon catheter may be an angioplasty catheter or a stent delivery catheter. Preferably, the inflatable balloon catheter is an angioplasty catheter. Preferably, the inflatable balloon catheter is used for treatment of restenosis in an artery.

In use, the inflatable balloon may be inflated by infusing fluid, such as water, saline or the like, into the inflatable balloon through, for example, a lumen of a catheter in communication with the interior surface of the inflatable balloon. In some embodiments, the fluid is at or above the heat transition temperature of the coating. For example, the fluid may be at or above the release transition temperature of the coating, such as 2° C. or more, 3° C. or more, or 5° C. or more above the release transition temperature of the coating. The fluid may be heated or maintained at a suitable temperature external to the patient prior to introduction into, for example, the lumen of the catheter. Until the fluid is introduced and while the coating is below the release transition temperature, the therapeutic agent is retained by the coating. When the fluid is introduced and the coating is heated to a temperature above the release transition temperature, the therapeutic agent is released from the coating. Accordingly, the therapeutic agent may advantageously be released while the inflatable balloon is inflated and in contact with tissue to be treated.

In some embodiments, an inflatable balloon catheter includes a heating element configured to heat the coating at or above its release transition temperature. Any suitable heating element may be employed. For example, a resistive element, such as a wire or pad, may be placed on an inner surface or outer surface of an inflatable balloon and electrically coupled with a controllable power source that may, optionally, remain external to a patient during a procedure in which the inflatable balloon catheter is used. By way of another example, an ultrasonic heating element may be placed, for example, in the inflatable balloon and may be coupled to an ultrasonic source that may, optionally, remain external to a patient during a procedure in which the inflatable balloon catheter is used. Another example includes an RF heating coil or a light induced heating element, such as an infrared, ultraviolet or P-N junction heating element. In still other embodiments, an infrared or ultraviolet light may be disposed within an interior space of the inflatable balloon. Once the inflatable balloon has been inflated, the infrared or ultraviolet light may be activated to heat the coating, and thus raise the coating above its transition temperature. For example, in embodiments, a fiber optic wire may extend along the catheter and into the interior space of the inflatable balloon, and the infrared or ultraviolet light may be transmitted through the fiber optic wire and into the interior space of the inflatable balloon.

Referring now to FIG. 1, a sectional view of an inflated inflatable balloon 100 is shown. The inflatable balloon 100 comprises a wall 110 defining an interior surface 102 and an exterior surface 103, the interior surface 102 defining an interior space 105. A coating 200 is disposed on the exterior surface 103 of the inflatable balloon 100. The depicted coating comprises two layers. The first layer 210 comprising a therapeutic agent is disposed on the exterior surface 103 of the inflatable balloon 100. A second layer 220 comprising a temperature-responsive polymer is disposed on the first layer 210.

Figure 2:
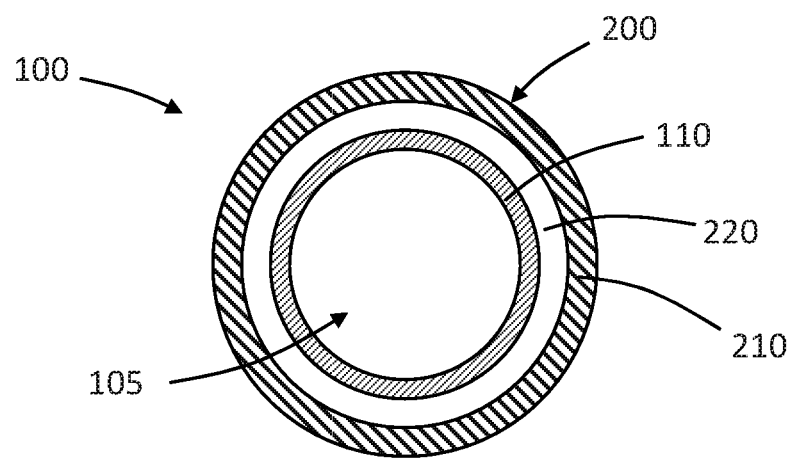

Referring now to FIG. 2, a sectional view of an inflated inflatable balloon 100 is shown. The inflatable balloon 100 comprises a wall 110 defining an interior surface 102 and an exterior surface 103, the interior surface 102 defining an interior space 105. A coating 200 is disposed on the exterior surface 103 of the inflatable balloon 100. The depicted coating comprises two layers. The first layer 220 comprising a temperature-responsive polymer is disposed on the exterior surface 103 of the inflatable balloon 100. A second layer 210 comprising a therapeutic agent is disposed on the first layer 220.

Figure 3:
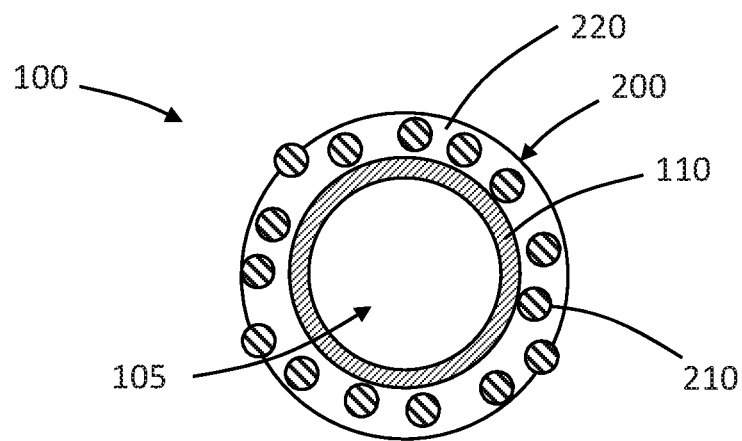

Referring now to FIG. 3, a sectional view of an inflated inflatable balloon 100 is shown. The inflatable balloon 100 comprises a wall 110 defining an interior surface 102 and an exterior surface 103, the interior surface 102 defining an interior space 105. A coating 200 is disposed on the exterior surface 103 of the inflatable balloon 100. The coating 200 comprises therapeutic agent 210 intermixed with a temperature-responsive polymer 220.

It will be understood that FIGS. 1-3 depict only some ways in which a thermo-responsive coating comprising a therapeutic agent may be disposed on an inflatable medical inflatable balloon and that other orientations are envisioned.

Figure 4:
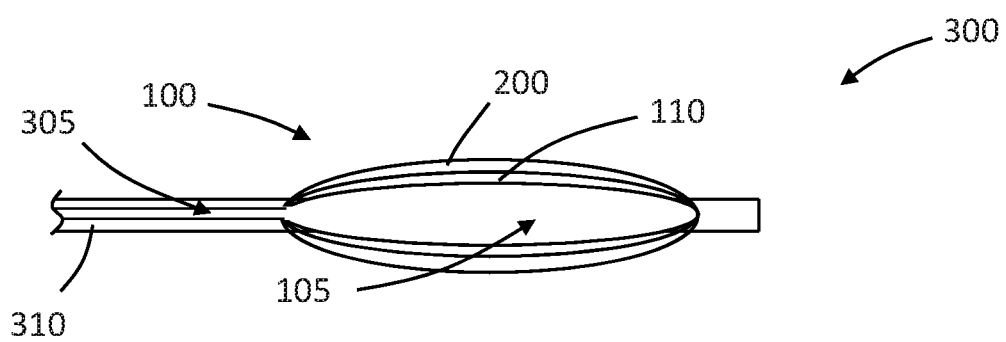
FIG. 4 is a schematic sectional view of an inflatable balloon catheter in accordance with various embodiments described herein.

Referring now to FIG. 4, a sectional view of an inflatable balloon catheter 300 is shown. The inflatable balloon catheter 300 includes a catheter 310 and an inflatable balloon 100 having a wall 110 defining an interior surface 102 and an exterior surface 103, the interior surface 102 defining an interior space 105. A coating 200, such as a coating described above regarding FIGS. 1-3, is disposed on the exterior surface 103 defined by the inflatable balloon wall 110. The catheter 310 defines a lumen 305 in communication with the interior space 105 of the inflatable balloon 100 for inflating the inflatable balloon 100.

Figure 5A:
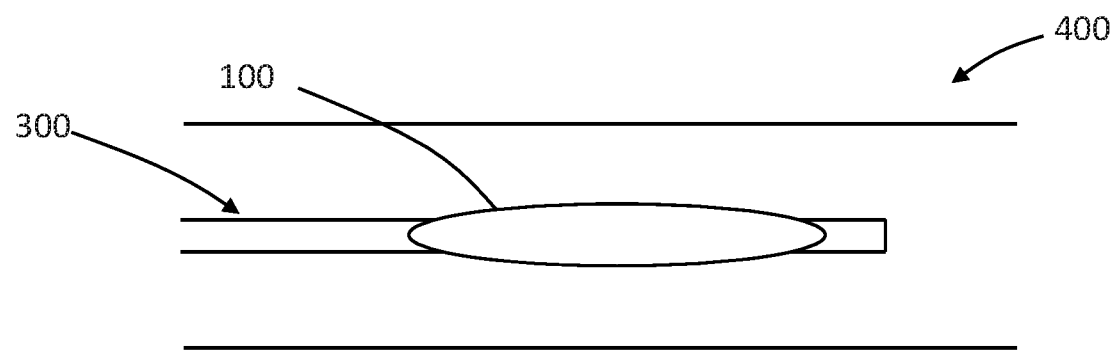
FIGS. 5A-B are schematic views of an inflatable balloon catheter in an artery in uninflated (FIG. 5A) and inflated (FIG. 5B) states in accordance with various embodiments described herein.
Figure 5B:
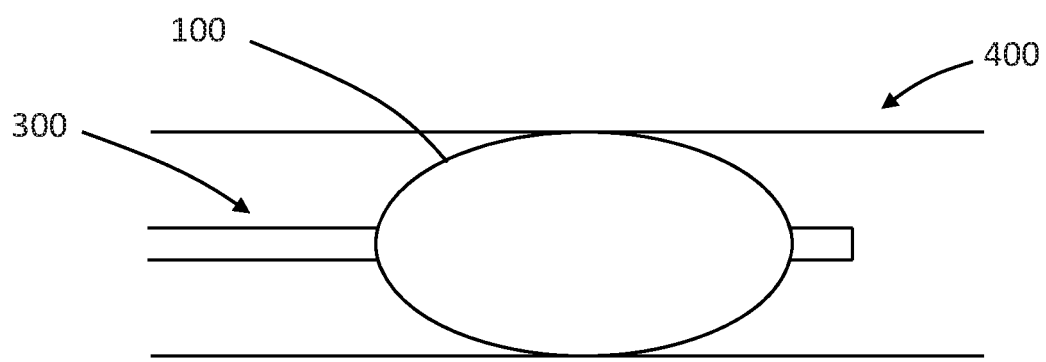

Referring now to FIGS. 5A-B, schematic drawings showing an inflatable balloon catheter 300 in a vessel 400 in uninflated (FIG. 5A) and inflated (FIG. 5B) states are shown. The inflatable balloon catheter 300 may be advanced within the vessel 400, such as an artery, until inflatable balloon 100 is aligned with a target site for intervention, such as a narrowing of the artery 400. The inflatable balloon 100 may be inflated (FIG. 5B) with fluid, for example, at a temperature above the release transition temperature of a coating (not shown) disposed on the inflatable balloon 100. The temperature of the fluid in the inflatable balloon 100 may cause the coating to release therapeutic agent (not shown) when the inflatable balloon 100 is inflated and in contact with the arterial wall.

Figure 6:
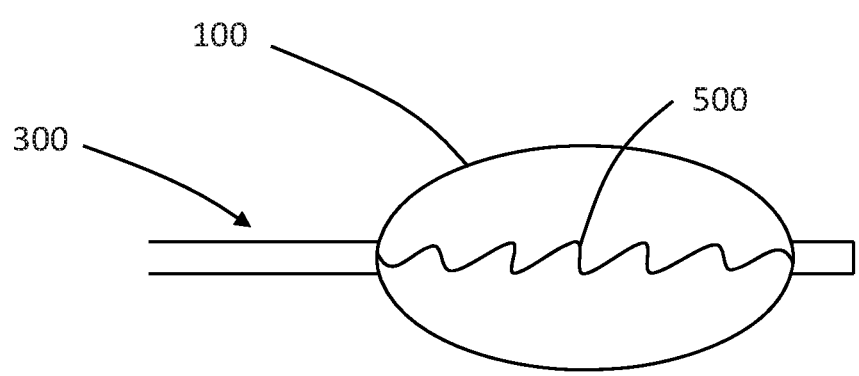
FIG. 6 is a side view of an inflatable balloon catheter having a heating element disposed on the inflatable balloon.

Referring now to FIG. 6, a schematic side view of an inflatable balloon catheter 300 including an inflatable balloon 100 and a heating element 500 disposed on the inflatable balloon 100. The heating element 500 may be used to cause a coating (not shown in FIG. 6) to heat above its release transition temperature to cause a therapeutic agent to be released from the coating. The heating element 500 may be, for example, a resistive element, an ultrasonic heating element, a RF heating element, or a light inducted heating element.

While described herein mainly in terms of treatment of restenosis in arteries, the balloon catheters described herein may be useful for treating other diseases in other passageways. For example, the balloon catheters described herein may be used in veins, coronary arteries, renal arteries, peripheral arteries including illiac arteries, arteries of the neck and cerebral arteries, and may also be advantageously employed in other body structures, including but not limited to arteries, veins, biliary ducts, urethras, fallopian tubes, bronchial tubes, the trachea, the esophagus and the prostate.

All scientific and technical terms used herein have meanings commonly used in the art unless otherwise specified. The definitions provided herein are to facilitate understanding of certain terms used frequently herein and are not meant to limit the scope of the present disclosure.

As used herein, singular forms "a," "an" and "the" include plural referents unless the context clearly dictates otherwise. Thus, for example, reference to a "layer" includes examples having two or more such "layers" unless the context clearly indicates otherwise.

As used in this specification and the appended claims, the term "or" is generally employed in its sense including "and/or" unless the content clearly dictates otherwise. The term "and/or" means one or all of the listed elements or a combination of any two or more of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the inventive technology.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

As used herein, "providing" in the context of providing an article for use in a method means to make, purchase, or otherwise obtain the article.

In the following, non-limiting examples of temperature-responsive coatings and therapeutic agents that may be employed with balloon catheters are described.

EXAMPLES

Example 1

Temperature Dependency Release of Paclitaxel from poly(N-isopropylacrylamide)

Coatings comprising poly(N-isopropylacrylamide) and paclitaxel were applied to a nylon 12 coupon and release of paclitaxel in an aqueous environment was tested. The amount of paclitaxel released generally increased with increasing temperatures. However, the amount of paclitaxel released from two different acrylamide coatings was markedly enhanced at higher temperatures relative to a control coating of paclitaxel alone. At 25° C., no appreciable amount of paclitaxel was released from any of the coating formulations, including the bare paclitaxel control. Paclitaxel release from the acrylamide coatings was greater at 37° C. than at 25° C. For one of acrylamide coatings paclitaxel release was greater at 37° C. than at 47° C., indicating a release transition temperature somewhere between 25° C. and 37° C.

The results indicate that it is possible to control the temperature at which paclitaxel is released from a coating and suggest that the release transition temperature may be tuned as desired.

It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

All patent application, patents, journal articles and other printed publications referred to herein are all each hereby incorporated herein in their respective entireties to the extent that they do no conflict with the disclosure presented herein.

What is claimed is:

1. A medical device comprising:
an inflatable angioplasty balloon defining an interior surface and an exterior surface, the interior surface defining an interior space; and
a coating disposed on the exterior surface of the inflatable balloon, the coating comprising a therapeutic agent,
wherein the coating has a release transition temperature within a range of 25° C. to 37° C.,
wherein, when the temperature of the coating is below the release transition temperature, at least a portion of the therapeutic agent is retained in the coating, and wherein, when the temperature of the coating is at the release transition temperature, at least a portion of the therapeutic agent is released from the coating.

2. The medical device of claim 1, wherein the coating comprises a first layer disposed on the exterior surface of the inflatable balloon and a second layer disposed on the first layer, wherein the second layer comprises the therapeutic agent.

3. The medical device of claim 1, wherein the coating comprises a first layer disposed on the exterior surface of the inflatable balloon and a second layer disposed on the first layer, wherein the first layer comprises the therapeutic agent.

4. The medical device of claim 1, wherein the coating comprises a polymer, and wherein the therapeutic agent and the polymer are intermixed in a layer disposed on the exterior surface of the inflatable balloon.

5. The medical device of claim 1, wherein the coating has a release transition temperature for the therapeutic agent within a range of about 30° C. to about 35° C.

6. The medical device of claim 1, wherein the coating has a release transition temperature for the therapeutic agent within a range of about 25° C. to about 30° C.

7. The medical device of claim 1, wherein the coating comprises a temperature-responsive hydrogel.

8. The medical device of claim 1, wherein the coating comprises poly(N-isopropylacrylamide), poly(N'N;-diethylacrylamide), an N-isopropylacrylamide copolymer, an N'N;-diethylacrylamide copolymer, or combinations thereof.

9. The medical device of claim 1, wherein the therapeutic agent comprises paclitaxel.

10. The medical device of claim 9, wherein the coating further comprises urea.

11. The medical device of claim 1, further comprising a catheter comprising a lumen in fluid communication with the interior space of the inflatable balloon.

12. The medical device of claim 1, further comprising a heating element configured to actively heat the coating such that the coating reaches the release transition temperature.

13. The medical device of claim 1, wherein the coating has a release transition temperature within a range of 25° C. to 35° C.

14. The medical device of claim 1, wherein the coating has a release transition temperature within a range of 30° C. to 35° C.

15. The medical device of claim 1, wherein the coating provides for release of the therapeutic agent in less than 2 minutes.

16. The medical device of claim 1, wherein the coating provides for release of the therapeutic agent in a time period from 30 seconds to one minute.

17. A method for coating an inflatable angioplasty balloon of a medical device, comprising:
applying a coating to an exterior surface of the inflatable balloon, wherein the coating comprises a therapeutic agent and a temperature-responsive polymer and wherein the coating has a release transition temperature within a range of 25° C. to 37° C., wherein the coating is configured to release at least a portion of the therapeutic agent at the release transition temperature.

18. The method of claim 17, wherein applying the coating comprises applying a composition comprising the polymer on the exterior surface of the inflatable balloon to form a first layer and applying a composition comprising the therapeutic agent on the first layer to form a second layer disposed on the first layer.

19. The method of claim 17, wherein applying the coating comprises applying a composition comprising the therapeutic agent on the exterior surface of the inflatable balloon to form a first layer and applying a composition comprising the polymer on the first layer to form a second layer disposed on the first layer.

20. The method of claim 17, wherein applying the coating comprises applying to the exterior surface of the inflatable balloon a composition comprising the therapeutic agent and the polymer.

21. The method of claim 17, wherein the coating has a release transition temperature within a range of 25° C. to 35° C.

22. The method of claim 17, wherein the coating has a release transition temperature within a range of 30° C. to 35° C.

23. The method of claim 17, wherein the coating provides for release of the therapeutic agent in less than 2 minutes.

24. The method of claim 17, wherein the coating provides for release of the therapeutic agent in a time period from 30 seconds to one minute.

25. The method of claim 17, wherein the coating provides for release of the therapeutic agent in less than 2 minutes.

26. The method of claim 17, wherein the coating provides for release of the therapeutic agent in a time period from 30 seconds to one minute.

27. A method comprising:
providing a medical device comprising:
an inflatable angioplasty balloon defining an interior surface and an exterior surface, the interior surface defining an interior space; and
a coating disposed on the exterior surface of the inflatable balloon, the coating comprising a therapeutic agent,
wherein the coating has a release transition temperature within a range of 25° C. to 37° C.,
wherein, when the temperature of the coating is below the release transition temperature, at least a portion of the therapeutic agent is retained in the coating, and
wherein, when the temperature of the coating is at the release transition temperature, at least a portion of the therapeutic agent is released from the coating;
inserting the inflatable balloon to a target location of a patient;
inflating the inflatable balloon by introducing a fluid into the interior space of the inflatable balloon; and
heating the coating disposed on the inflatable balloon such that the coating reaches the release transition temperature,
wherein inflating the inflatable balloon causes the inflatable balloon to expand against tissue of the patient to transfer the therapeutic agent to the tissue.

28. The method of claim 27, wherein the coating has a release transition temperature within a range of 25° C. to 35° C.

29. The method of claim 27, wherein the coating has a release transition temperature within a range of 30° C. to 35° C.

* * * * *